United States Patent
Long et al.

(10) Patent No.: US 8,114,072 B2
(45) Date of Patent: Feb. 14, 2012

(54) ELECTRICAL ABLATION DEVICE

(75) Inventors: Gary L. Long, Cincinnati, OH (US); Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 898 days.

(21) Appl. No.: 12/130,010

(22) Filed: May 30, 2008

(65) Prior Publication Data
US 2009/0299362 A1    Dec. 3, 2009

(51) Int. Cl.
*A61B 18/18* (2006.01)
(52) U.S. Cl. ............................................. 606/37; 606/39
(58) Field of Classification Search .......... 600/564–568; 606/37, 39, 159, 167
See application file for complete search history.

(56) References Cited

U.S. PATENT DOCUMENTS

| | | |
|---|---|---|
| 645,576 A | 3/1900 | Tesla |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |

(Continued)

FOREIGN PATENT DOCUMENTS
AU     666310 B2     2/1996
(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Linda Dvorak
*Assistant Examiner* — Brian M Antiskay

(57) ABSTRACT

An electrical ablation apparatus includes a housing extending along a longitudinal axis. A first electrode and a second electrode are disposed within the housing. The electrodes are configured to connect to electrically conductive wires. The first and second electrodes are separated by a gap. The second electrode includes first and second prongs defining an opening suitable to receive tissue to be ablated therebetween. When the first and second electrodes are energized at a predetermined energy level, an electric current suitable to ablate the tissue flows across the gap and forms an electric arc between the distal end of the first electrode and the tissue. A system includes an energy source to drive the electrical ablation apparatus. A method includes introducing the electrical ablation apparatus into a patient and ablating tissue with the electric arc.

18 Claims, 9 Drawing Sheets

U.S. PATENT DOCUMENTS

| | | | |
|---|---|---|---|
| 3,946,740 A | 3/1976 | Bassett | |
| 3,948,251 A | 4/1976 | Hosono | |
| 3,994,301 A | 11/1976 | Agris | |
| 4,011,872 A * | 3/1977 | Komiya | 606/47 |
| 4,012,812 A | 3/1977 | Black | |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,977,887 A | 12/1990 | Gouda | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A | 2/1994 | Wilk | |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,374,273 A | 12/1994 | Nakao et al. | |
| 5,374,275 A | 12/1994 | Bradley et al. | |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A | 5/1995 | Klein et al. | |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,499 A | 8/1995 | Fritzsch | |
| 5,449,021 A | 9/1995 | Chikama | |
| 5,456,667 A | 10/1995 | Ham et al. | |
| 5,456,684 A | 10/1995 | Schmidt et al. | |
| 5,458,131 A | 10/1995 | Wilk | |
| 5,458,583 A | 10/1995 | McNeely et al. | |
| 5,460,168 A | 10/1995 | Masubuchi et al. | |
| 5,460,629 A | 10/1995 | Shlain et al. | |
| 5,462,561 A | 10/1995 | Voda | |
| 5,465,731 A | 11/1995 | Bell et al. | |
| 5,467,763 A | 11/1995 | McMahon et al. | |

| Patent No. | Date | Inventor(s) | Patent No. | Date | Inventor(s) |
|---|---|---|---|---|---|
| 5,468,250 A | 11/1995 | Paraschac et al. | 5,766,170 A | 6/1998 | Eggers |
| 5,470,308 A | 11/1995 | Edwards et al. | 5,766,205 A | 6/1998 | Zvenyatsky et al. |
| 5,470,320 A | 11/1995 | Tiefenbrun et al. | 5,769,849 A | 6/1998 | Eggers |
| 5,478,347 A | 12/1995 | Aranyi | 5,779,701 A | 7/1998 | McBrayer et al. |
| 5,480,404 A | 1/1996 | Kammerer et al. | 5,779,716 A | 7/1998 | Cano et al. |
| 5,482,054 A | 1/1996 | Slater et al. | 5,779,727 A | 7/1998 | Orejola |
| 5,484,451 A | 1/1996 | Akopov et al. | 5,782,859 A | 7/1998 | Nicholas et al. |
| 5,489,256 A | 2/1996 | Adair | 5,782,866 A | 7/1998 | Wenstrom, Jr. |
| 5,496,347 A | 3/1996 | Hashiguchi et al. | 5,791,022 A | 8/1998 | Bohman |
| 5,499,990 A | 3/1996 | Schülken et al. | 5,792,113 A | 8/1998 | Kramer et al. |
| 5,499,992 A | 3/1996 | Meade et al. | 5,792,153 A | 8/1998 | Swain et al. |
| 5,501,692 A | 3/1996 | Riza | 5,792,165 A | 8/1998 | Klieman et al. |
| 5,503,616 A | 4/1996 | Jones | 5,797,835 A | 8/1998 | Green |
| 5,505,686 A | 4/1996 | Willis et al. | 5,797,928 A | 8/1998 | Kogasaka |
| 5,507,755 A | 4/1996 | Gresl et al. | 5,797,939 A | 8/1998 | Yoon |
| 5,511,564 A | 4/1996 | Wilk | 5,797,941 A | 8/1998 | Schulze et al. |
| 5,514,157 A | 5/1996 | Nicholas et al. | 5,803,903 A | 9/1998 | Athas et al. |
| 5,522,829 A | 6/1996 | Michalos | 5,808,665 A | 9/1998 | Green |
| 5,522,830 A | 6/1996 | Aranyi | 5,810,806 A | 9/1998 | Ritchart et al. |
| 5,527,321 A | 6/1996 | Hinchliffe | 5,810,849 A | 9/1998 | Kontos |
| 5,540,648 A | 7/1996 | Yoon | 5,810,865 A | 9/1998 | Koscher et al. |
| 5,554,151 A | 9/1996 | Hinchliffe | 5,810,876 A | 9/1998 | Kelleher |
| 5,555,883 A | 9/1996 | Avitall | 5,810,877 A | 9/1998 | Roth et al. |
| 5,558,133 A | 9/1996 | Bortoli et al. | 5,813,976 A | 9/1998 | Filipi et al. |
| 5,562,693 A | 10/1996 | Devlin et al. | 5,814,058 A | 9/1998 | Carlson et al. |
| 5,569,243 A | 10/1996 | Kortenbach et al. | 5,817,061 A | 10/1998 | Goodwin et al. |
| 5,569,298 A | 10/1996 | Schnell | 5,817,107 A | 10/1998 | Schaller |
| 5,573,540 A | 11/1996 | Yoon | 5,817,119 A | 10/1998 | Klieman et al. |
| 5,578,030 A | 11/1996 | Levin | 5,819,736 A | 10/1998 | Avny et al. |
| 5,582,611 A | 12/1996 | Tsuruta et al. | 5,827,281 A | 10/1998 | Levin |
| 5,582,617 A | 12/1996 | Klieman et al. | 5,827,299 A | 10/1998 | Thomason et al. |
| 5,584,845 A | 12/1996 | Hart | 5,830,231 A | 11/1998 | Geiges, Jr. |
| 5,591,179 A | 1/1997 | Edelstein | 5,833,700 A | 11/1998 | Fogelberg et al. |
| 5,593,420 A | 1/1997 | Eubanks, Jr. et al. | 5,833,703 A | 11/1998 | Manushakian |
| 5,595,562 A | 1/1997 | Grier | 5,843,017 A | 12/1998 | Yoon |
| 5,597,378 A | 1/1997 | Jervis | 5,849,022 A | 12/1998 | Sakashita et al. |
| 5,601,573 A | 2/1997 | Fogelberg et al. | 5,853,374 A | 12/1998 | Hart et al. |
| 5,601,588 A | 2/1997 | Tonomura et al. | 5,855,585 A | 1/1999 | Kontos |
| 5,604,531 A | 2/1997 | Iddan et al. | 5,860,913 A | 1/1999 | Yamaya et al. |
| 5,607,389 A | 3/1997 | Edwards et al. | 5,860,995 A | 1/1999 | Berkelaar |
| 5,607,450 A | 3/1997 | Zvenyatsky et al. | 5,868,762 A | 2/1999 | Cragg et al. |
| 5,613,975 A | 3/1997 | Christy | 5,876,411 A | 3/1999 | Kontos |
| 5,618,303 A | 4/1997 | Marlow et al. | 5,882,331 A | 3/1999 | Sasaki |
| 5,620,415 A | 4/1997 | Lucey et al. | 5,882,344 A | 3/1999 | Stouder, Jr. |
| 5,624,399 A | 4/1997 | Ackerman | 5,893,846 A | 4/1999 | Bales et al. |
| 5,624,431 A | 4/1997 | Gerry et al. | 5,893,874 A | 4/1999 | Bourque et al. |
| 5,628,732 A | 5/1997 | Antoon, Jr. et al. | 5,893,875 A | 4/1999 | O'Connor et al. |
| 5,630,782 A | 5/1997 | Adair | 5,899,919 A | 5/1999 | Eubanks, Jr. et al. |
| 5,643,283 A | 7/1997 | Younker | 5,902,254 A | 5/1999 | Magram |
| 5,643,292 A | 7/1997 | Hart | 5,904,702 A | 5/1999 | Ek et al. |
| 5,643,294 A | 7/1997 | Tovey et al. | 5,908,420 A | 6/1999 | Parins et al. |
| 5,644,798 A | 7/1997 | Shah | 5,916,147 A | 6/1999 | Boury |
| 5,645,083 A | 7/1997 | Essig et al. | 5,921,993 A | 7/1999 | Yoon |
| 5,649,372 A | 7/1997 | Souza | 5,921,997 A | 7/1999 | Fogelberg et al. |
| 5,653,677 A | 8/1997 | Okada et al. | 5,922,008 A | 7/1999 | Gimpelson |
| 5,653,722 A | 8/1997 | Kieturakis | 5,925,052 A | 7/1999 | Simmons |
| 5,662,663 A | 9/1997 | Shallman | 5,928,255 A | 7/1999 | Meade et al. |
| 5,669,875 A | 9/1997 | van Eerdenburg | 5,928,266 A | 7/1999 | Kontos |
| 5,681,324 A | 10/1997 | Kammerer et al. | 5,936,536 A | 8/1999 | Morris |
| 5,681,330 A | 10/1997 | Hughett et al. | 5,944,718 A | 8/1999 | Austin et al. |
| 5,685,820 A | 11/1997 | Riek et al. | 5,951,549 A | 9/1999 | Richardson et al. |
| 5,690,656 A | 11/1997 | Cope et al. | 5,954,720 A | 9/1999 | Wilson et al. |
| 5,690,660 A | 11/1997 | Kauker et al. | 5,954,731 A | 9/1999 | Yoon |
| 5,695,448 A | 12/1997 | Kimura et al. | 5,957,943 A | 9/1999 | Vaitekunas |
| 5,695,505 A | 12/1997 | Yoon | 5,957,953 A | 9/1999 | DiPoto et al. |
| 5,695,511 A | 12/1997 | Cano et al. | 5,971,995 A | 10/1999 | Rousseau |
| 5,700,275 A | 12/1997 | Bell et al. | 5,976,074 A | 11/1999 | Moriyama |
| 5,704,892 A | 1/1998 | Adair | 5,976,075 A | 11/1999 | Beane et al. |
| 5,709,708 A | 1/1998 | Thal | 5,976,130 A | 11/1999 | McBrayer et al. |
| 5,716,326 A | 2/1998 | Dannan | 5,976,131 A | 11/1999 | Guglielmi et al. |
| 5,730,740 A | 3/1998 | Wales et al. | 5,980,539 A | 11/1999 | Kontos |
| 5,741,278 A | 4/1998 | Stevens | 5,980,556 A | 11/1999 | Giordano et al. |
| 5,741,285 A | 4/1998 | McBrayer et al. | 5,984,938 A | 11/1999 | Yoon |
| 5,746,759 A | 5/1998 | Meade et al. | 5,989,182 A | 11/1999 | Hori et al. |
| 5,749,881 A | 5/1998 | Sackier et al. | 5,993,447 A | 11/1999 | Blewett et al. |
| 5,749,889 A | 5/1998 | Bacich et al. | 5,997,555 A | 12/1999 | Kontos |
| 5,752,951 A | 5/1998 | Yanik | 6,001,120 A | 12/1999 | Levin |
| 5,755,731 A | 5/1998 | Grinberg | 6,004,330 A | 12/1999 | Middleman et al. |
| 5,766,167 A | 6/1998 | Eggers et al. | 6,007,566 A | 12/1999 | Wenstrom, Jr. |

| | | | |
|---|---|---|---|
| 6,010,515 A | 1/2000 | Swain et al. | |
| 6,012,494 A | 1/2000 | Balazs | |
| 6,019,770 A | 2/2000 | Christoudias | |
| 6,024,708 A | 2/2000 | Bales et al. | |
| 6,024,747 A | 2/2000 | Kontos | |
| 6,027,522 A | 2/2000 | Palmer | |
| 6,030,365 A | 2/2000 | Laufer | |
| 6,033,399 A | 3/2000 | Gines | |
| 6,053,927 A | 4/2000 | Hamas | |
| 6,066,160 A | 5/2000 | Colvin et al. | |
| 6,068,603 A | 5/2000 | Suzuki | |
| 6,068,629 A | 5/2000 | Haissaguerre et al. | |
| 6,071,233 A | 6/2000 | Ishikawa et al. | |
| 6,074,408 A | 6/2000 | Freeman | |
| 6,086,530 A | 7/2000 | Mack | |
| 6,090,108 A | 7/2000 | McBrayer et al. | |
| 6,096,046 A | 8/2000 | Weiss | |
| 6,110,154 A | 8/2000 | Shimomura et al. | |
| 6,110,183 A | 8/2000 | Cope | |
| 6,113,593 A | 9/2000 | Tu et al. | |
| 6,117,144 A | 9/2000 | Nobles et al. | |
| 6,117,158 A | 9/2000 | Measamer et al. | |
| 6,139,555 A | 10/2000 | Hart et al. | |
| 6,146,391 A | 11/2000 | Cigaina | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1 | 5/2001 | Marchand | |
| 6,245,079 B1 | 6/2001 | Nobles et al. | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,543 B1 | 3/2002 | Cole | |
| 6,355,035 B1 | 3/2002 | Manushakian | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,391,029 B1 | 5/2002 | Hooven et al. | |
| 6,402,735 B1 | 6/2002 | Langevin | |
| 6,406,440 B1 | 6/2002 | Stefanchik | |
| 6,409,733 B1 | 6/2002 | Conlon et al. | |
| 6,431,500 B1 | 8/2002 | Jacobs et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,464,701 B1 | 10/2002 | Hooven et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,691 B1 | 12/2002 | Morley et al. | |
| 6,493,590 B1 | 12/2002 | Wessman et al. | |
| 6,494,893 B2 | 12/2002 | Dubrul et al. | |
| 6,503,192 B1 | 1/2003 | Ouchi | |
| 6,506,190 B1 | 1/2003 | Walshe | |
| 6,508,827 B1 | 1/2003 | Manhes | |
| 6,543,456 B1 | 4/2003 | Freeman | |
| 6,551,270 B1 | 4/2003 | Bimbo et al. | |
| 6,554,829 B2 | 4/2003 | Schulze et al. | |
| 6,558,384 B2 | 5/2003 | Mayenberger | |
| 6,562,035 B1 | 5/2003 | Levin | |
| 6,562,052 B2 | 5/2003 | Nobles et al. | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,579,311 B1 | 6/2003 | Makower | |
| 6,585,642 B2 | 7/2003 | Christopher | |
| 6,585,717 B1 | 7/2003 | Wittenberger et al. | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,626,919 B1 | 9/2003 | Swanstrom | |
| 6,632,229 B1 | 10/2003 | Yamanouchi | |
| 6,638,286 B1 | 10/2003 | Burbank et al. | |
| 6,652,521 B2 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,666,854 B1 | 12/2003 | Lange | |
| 6,672,338 B1 | 1/2004 | Esashi et al. | |
| 6,673,087 B1 | 1/2004 | Chang et al. | |
| 6,685,628 B2 | 2/2004 | Vu | |
| 6,685,724 B1 | 2/2004 | Haluck | |
| 6,692,445 B2 | 2/2004 | Roberts et al. | |
| 6,692,462 B2 | 2/2004 | Mackenzie et al. | |
| 6,699,180 B2 | 3/2004 | Kobayashi | |
| 6,699,256 B1 | 3/2004 | Logan et al. | |
| 6,699,263 B2 | 3/2004 | Cope | |
| 6,708,066 B2 | 3/2004 | Herbst et al. | |
| 6,716,226 B2 | 4/2004 | Sixto, Jr. et al. | |
| 6,740,030 B2 | 5/2004 | Martone et al. | |
| 6,743,240 B2 | 6/2004 | Smith et al. | |
| 6,749,560 B1 | 6/2004 | Konstorum et al. | |
| 6,749,609 B1 | 6/2004 | Lunsford et al. | |
| 6,752,768 B2 | 6/2004 | Burdorff et al. | |
| 6,752,811 B2 | 6/2004 | Chu et al. | |
| 6,752,822 B2 | 6/2004 | Jespersen | |
| 6,761,685 B2 | 7/2004 | Adams et al. | |
| 6,761,718 B2 * | 7/2004 | Madsen .................... 606/50 |
| 6,773,434 B2 | 8/2004 | Ciarrocca | |
| 6,780,151 B2 | 8/2004 | Grabover et al. | |
| 6,780,352 B2 | 8/2004 | Jacobson | |
| 6,783,491 B2 | 8/2004 | Saadat et al. | |
| 6,786,864 B2 | 9/2004 | Matsuura et al. | |
| 6,790,173 B2 | 9/2004 | Saadat et al. | |
| 6,795,728 B2 | 9/2004 | Chornenky et al. | |
| 6,800,056 B2 | 10/2004 | Tartaglia et al. | |
| 6,808,491 B2 | 10/2004 | Kortenbach et al. | |
| 6,824,548 B2 | 11/2004 | Smith et al. | |
| 6,837,847 B2 | 1/2005 | Ewers et al. | |
| 6,843,794 B2 | 1/2005 | Sixto, Jr. et al. | |
| 6,861,250 B2 | 3/2005 | Cole et al. | |
| 6,866,627 B2 | 3/2005 | Nozue | |
| 6,878,106 B1 | 4/2005 | Herrmann | |
| 6,878,110 B2 | 4/2005 | Yang et al. | |
| 6,884,213 B2 | 4/2005 | Raz et al. | |
| 6,887,255 B2 | 5/2005 | Shimm | |
| 6,896,683 B1 | 5/2005 | Gadberry et al. | |
| 6,908,427 B2 | 6/2005 | Fleener et al. | |
| 6,908,476 B2 | 6/2005 | Jud et al. | |
| 6,916,284 B2 | 7/2005 | Moriyama | |
| 6,918,871 B2 | 7/2005 | Schulze | |
| 6,926,725 B2 | 8/2005 | Cooke et al. | |
| 6,932,810 B2 | 8/2005 | Ryan | |

| Patent Number | Date | Inventor(s) |
|---|---|---|
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |

| | | | |
|---|---|---|---|
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1* | 5/2004 | Kuroshima et al. ............ 422/297 |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |

| | | | | | |
|---|---|---|---|---|---|
| 2006/0135984 A1 | 6/2006 | Kramer et al. | 2007/0112425 A1 | 5/2007 | Schaller et al. |
| 2006/0142644 A1 | 6/2006 | Mulac et al. | 2007/0118115 A1 | 5/2007 | Artale et al. |
| 2006/0142652 A1 | 6/2006 | Keenan | 2007/0123840 A1 | 5/2007 | Cox |
| 2006/0142790 A1 | 6/2006 | Gertner | 2007/0129605 A1 | 6/2007 | Schaaf |
| 2006/0142798 A1 | 6/2006 | Holman et al. | 2007/0129719 A1 | 6/2007 | Kendale et al. |
| 2006/0149132 A1 | 7/2006 | Iddan | 2007/0135709 A1 | 6/2007 | Rioux et al. |
| 2006/0149135 A1 | 7/2006 | Paz | 2007/0142706 A1 | 6/2007 | Matsui et al. |
| 2006/0161190 A1 | 7/2006 | Gadberry et al. | 2007/0156127 A1 | 7/2007 | Rioux et al. |
| 2006/0167416 A1 | 7/2006 | Mathis et al. | 2007/0161855 A1 | 7/2007 | Mikkaichi et al. |
| 2006/0167482 A1 | 7/2006 | Swain et al. | 2007/0173691 A1 | 7/2007 | Yokoi et al. |
| 2006/0178560 A1 | 8/2006 | Saadat et al. | 2007/0173869 A1 | 7/2007 | Gannoe et al. |
| 2006/0183975 A1 | 8/2006 | Saadat et al. | 2007/0173870 A2 | 7/2007 | Zacharias |
| 2006/0184161 A1 | 8/2006 | Maahs et al. | 2007/0173872 A1 | 7/2007 | Neuenfeldt |
| 2006/0189844 A1 | 8/2006 | Tien | 2007/0179525 A1 | 8/2007 | Frecker et al. |
| 2006/0189845 A1 | 8/2006 | Maahs et al. | 2007/0179530 A1 | 8/2007 | Tieu et al. |
| 2006/0190027 A1 | 8/2006 | Downey | 2007/0197865 A1 | 8/2007 | Miyake et al. |
| 2006/0195084 A1 | 8/2006 | Slater | 2007/0203487 A1 | 8/2007 | Sugita |
| 2006/0200005 A1 | 9/2006 | Bjork et al. | 2007/0208364 A1 | 9/2007 | Smith et al. |
| 2006/0200169 A1 | 9/2006 | Sniffin | 2007/0213754 A1 | 9/2007 | Mikkaichi et al. |
| 2006/0200170 A1 | 9/2006 | Aranyi | 2007/0225554 A1 | 9/2007 | Maseda et al. |
| 2006/0200199 A1 | 9/2006 | Bonutti et al. | 2007/0233040 A1 | 10/2007 | Macnamara et al. |
| 2006/0217665 A1 | 9/2006 | Prosek | 2007/0244358 A1 | 10/2007 | Lee |
| 2006/0217697 A1 | 9/2006 | Lau et al. | 2007/0250057 A1 | 10/2007 | Nobis et al. |
| 2006/0217742 A1 | 9/2006 | Messerly et al. | 2007/0255096 A1 | 11/2007 | Stefanchik et al. |
| 2006/0217743 A1 | 9/2006 | Messerly et al. | 2007/0255100 A1 | 11/2007 | Barlow et al. |
| 2006/0229639 A1 | 10/2006 | Whitfield | 2007/0255273 A1 | 11/2007 | Fernandez et al. |
| 2006/0229640 A1 | 10/2006 | Whitfield | 2007/0255303 A1 | 11/2007 | Bakos et al. |
| 2006/0237022 A1 | 10/2006 | Chen et al. | 2007/0255306 A1 | 11/2007 | Conlon et al. |
| 2006/0237023 A1 | 10/2006 | Cox et al. | 2007/0260112 A1 | 11/2007 | Rahmani |
| 2006/0241570 A1 | 10/2006 | Wilk | 2007/0260117 A1 | 11/2007 | Zwolinski et al. |
| 2006/0247576 A1 | 11/2006 | Poncet | 2007/0260121 A1 | 11/2007 | Bakos et al. |
| 2006/0247673 A1 | 11/2006 | Voegele et al. | 2007/0260273 A1 | 11/2007 | Cropper et al. |
| 2006/0253004 A1 | 11/2006 | Frisch et al. | 2007/0270629 A1 | 11/2007 | Charles |
| 2006/0253039 A1 | 11/2006 | McKenna et al. | 2007/0270889 A1 | 11/2007 | Conlon et al. |
| 2006/0258907 A1 | 11/2006 | Stefanchik et al. | 2007/0270895 A1 | 11/2007 | Nobis et al. |
| 2006/0258908 A1 | 11/2006 | Stefanchik et al. | 2007/0270907 A1 | 11/2007 | Stokes et al. |
| 2006/0258910 A1 | 11/2006 | Stefanchik et al. | 2007/0282371 A1 | 12/2007 | Lee et al. |
| 2006/0258954 A1 | 11/2006 | Timberlake et al. | 2007/0299387 A1 | 12/2007 | Williams et al. |
| 2006/0258955 A1 | 11/2006 | Hoffman et al. | 2008/0004650 A1 | 1/2008 | George |
| 2006/0259010 A1 | 11/2006 | Stefanchik et al. | 2008/0015409 A1 | 1/2008 | Barlow et al. |
| 2006/0264752 A1 | 11/2006 | Rubinsky et al. | 2008/0015552 A1 | 1/2008 | Doyle et al. |
| 2006/0264904 A1 | 11/2006 | Kerby et al. | 2008/0027387 A1 | 1/2008 | Grabinsky |
| 2006/0264930 A1 | 11/2006 | Nishimura | 2008/0033451 A1 | 2/2008 | Rieber et al. |
| 2006/0270902 A1 | 11/2006 | Igarashi et al. | 2008/0051629 A1 | 2/2008 | Sugiyama et al. |
| 2006/0271102 A1 | 11/2006 | Bosshard et al. | 2008/0051735 A1 | 2/2008 | Measamer et al. |
| 2006/0276835 A1 | 12/2006 | Uchida | 2008/0058586 A1 | 3/2008 | Karpiel |
| 2006/0281970 A1 | 12/2006 | Stokes et al. | 2008/0065169 A1 | 3/2008 | Colliou et al. |
| 2006/0282106 A1 | 12/2006 | Cole et al. | 2008/0086172 A1 | 4/2008 | Martin et al. |
| 2006/0285732 A1 | 12/2006 | Horn et al. | 2008/0097472 A1 | 4/2008 | Agmon et al. |
| 2006/0287644 A1 | 12/2006 | Inganas et al. | 2008/0097483 A1 | 4/2008 | Ortiz et al. |
| 2006/0287666 A1 | 12/2006 | Saadat et al. | 2008/0103527 A1 | 5/2008 | Martin et al. |
| 2006/0293626 A1 | 12/2006 | Byrum et al. | 2008/0114384 A1 | 5/2008 | Chang et al. |
| 2007/0002135 A1 | 1/2007 | Glukhovsky | 2008/0119870 A1 | 5/2008 | Williams |
| 2007/0005019 A1 | 1/2007 | Okishige | 2008/0125796 A1 | 5/2008 | Graham |
| 2007/0015965 A1 | 1/2007 | Cox et al. | 2008/0132892 A1 | 6/2008 | Lunsford et al. |
| 2007/0016225 A1 | 1/2007 | Nakao | 2008/0139882 A1 | 6/2008 | Fujimori |
| 2007/0032700 A1 | 2/2007 | Fowler et al. | 2008/0147113 A1 | 6/2008 | Nobis et al. |
| 2007/0032701 A1 | 2/2007 | Fowler et al. | 2008/0171907 A1 | 7/2008 | Long et al. |
| 2007/0043261 A1 | 2/2007 | Watanabe et al. | 2008/0188868 A1 | 8/2008 | Weitzner et al. |
| 2007/0043345 A1 | 2/2007 | Davalos et al. | 2008/0200755 A1 | 8/2008 | Bakos |
| 2007/0049800 A1 | 3/2007 | Boulais | 2008/0200762 A1 | 8/2008 | Stokes et al. |
| 2007/0049902 A1 | 3/2007 | Griffin et al. | 2008/0200911 A1 | 8/2008 | Long |
| 2007/0051375 A1 | 3/2007 | Milliman | 2008/0200912 A1 | 8/2008 | Long |
| 2007/0060880 A1 | 3/2007 | Gregorich et al. | 2008/0200933 A1 | 8/2008 | Bakos et al. |
| 2007/0067017 A1 | 3/2007 | Trapp | 2008/0200934 A1 | 8/2008 | Fox |
| 2007/0073102 A1 | 3/2007 | Matsuno et al. | 2008/0208213 A1 | 8/2008 | Benjamin et al. |
| 2007/0073269 A1 | 3/2007 | Becker | 2008/0221587 A1 | 9/2008 | Schwartz |
| 2007/0079924 A1 | 4/2007 | Saadat et al. | 2008/0221619 A1 | 9/2008 | Spivey et al. |
| 2007/0088370 A1 | 4/2007 | Kahle et al. | 2008/0228213 A1 | 9/2008 | Blakeney et al. |
| 2007/0100375 A1 | 5/2007 | Mikkaichi et al. | 2008/0230972 A1 | 9/2008 | Ganley |
| 2007/0100376 A1 | 5/2007 | Mikkaichi et al. | 2008/0234696 A1 | 9/2008 | Taylor et al. |
| 2007/0106118 A1 | 5/2007 | Moriyama | 2008/0243106 A1 | 10/2008 | Coe et al. |
| 2007/0112251 A1 | 5/2007 | Nakhuda | 2008/0243148 A1 | 10/2008 | Mikkaichi et al. |
| 2007/0112331 A1 | 5/2007 | Weber et al. | 2008/0243176 A1 | 10/2008 | Weitzner et al. |
| 2007/0112342 A1 | 5/2007 | Pearson et al. | 2008/0262540 A1 | 10/2008 | Bangera et al. |
| 2007/0112383 A1 | 5/2007 | Conlon et al. | 2008/0269782 A1 | 10/2008 | Stefanchik et al. |
| 2007/0112384 A1 | 5/2007 | Conlon et al. | 2008/0269783 A1 | 10/2008 | Griffith |
| 2007/0112385 A1 | 5/2007 | Conlon | 2008/0275474 A1 | 11/2008 | Martin et al. |
| 2007/0112417 A1 | 5/2007 | Shanley et al. | 2008/0275475 A1 | 11/2008 | Schwemberger et al. |

| | | |
|---|---|---|
| 2008/0287737 A1 | 11/2008 | Dejima |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2403909 A | 1/2005 |
| GB | 2421190 A | 6/2006 |

| | | |
|---|---|---|
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2005 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 01/10319 A1 | 2/2001 |
| WO | WO 01/41627 A2 | 6/2001 |
| WO | WO 01/58360 A | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastomosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastomotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).

U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/202,740, filed Sep. 2, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.

International Search Report and Written Opinion for PCT/US2009/045566, Oct. 29, 2009 (16 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.

U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.

International Preliminary Report on Patentability for PCT/US2009/045566, Nov. 30, 2010 (9 pages).
OCTO Port Modular Laparoscopy System for SIngle Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

* cited by examiner

ELECTRICAL ABLATION DEVICE

BACKGROUND

Electrical ablation has been employed in medicine to remove certain abnormal tissues or growths, such as cancers or tumors, from the body. Electrodes attached to therapy probes are positioned in proximity to or in contact with the diseased tissue. The electrodes are then energized by an energy source to remove the abnormal tissue. Conventional electrical therapy probes, however, are not effective for ablating or cutting through certain types of abnormal tissues such as adhesions, which develop in a majority of patients after surgery. Adhesions can be challenging to ablate using conventional electrical ablation therapy techniques. Thus, there is a need for electrical ablation devices that are suitable for ablating a variety of abnormal tissues, including adhesions and other abnormal fibrous growths. There is a further need for such electrical ablation devices to be introduced into the treatment region using minimally invasive surgical techniques.

FIGURES

The novel features of the various embodiments are set forth with particularity in the appended claims. The various embodiments, however, both as to organization and methods of operation, together with the advantages thereof, may be understood by reference to the following description taken in conjunction with the accompanying drawings as follows.

DESCRIPTION

Figure 1:
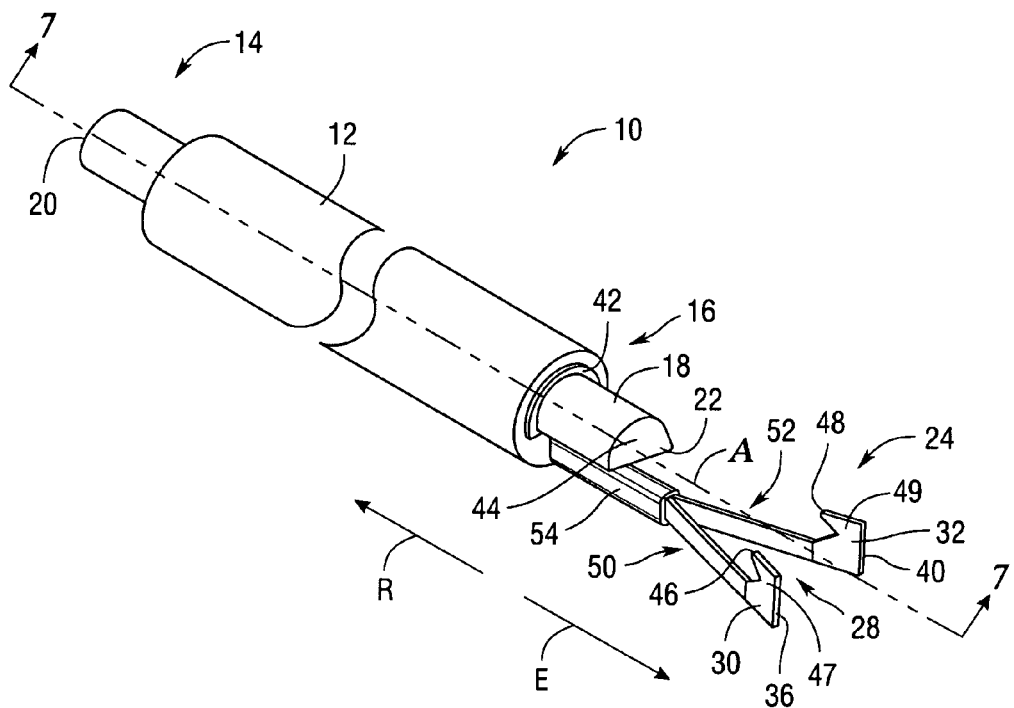
FIG. 1 is a perspective view of one embodiment of an electrical ablation apparatus with first and second electrodes in an extended position.
Figure 2:
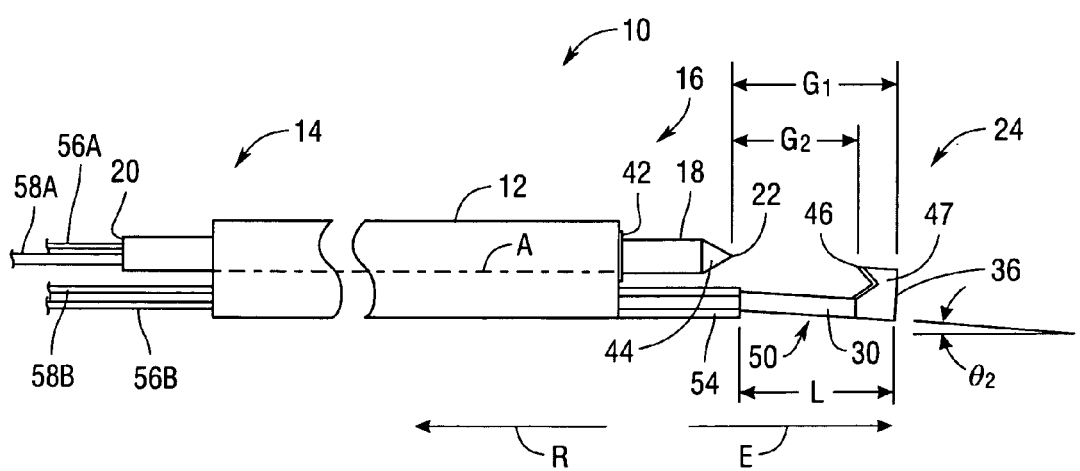
FIG. 2 is a side view of one embodiment of the electrical ablation apparatus shown in FIG. 1.
Figure 3:
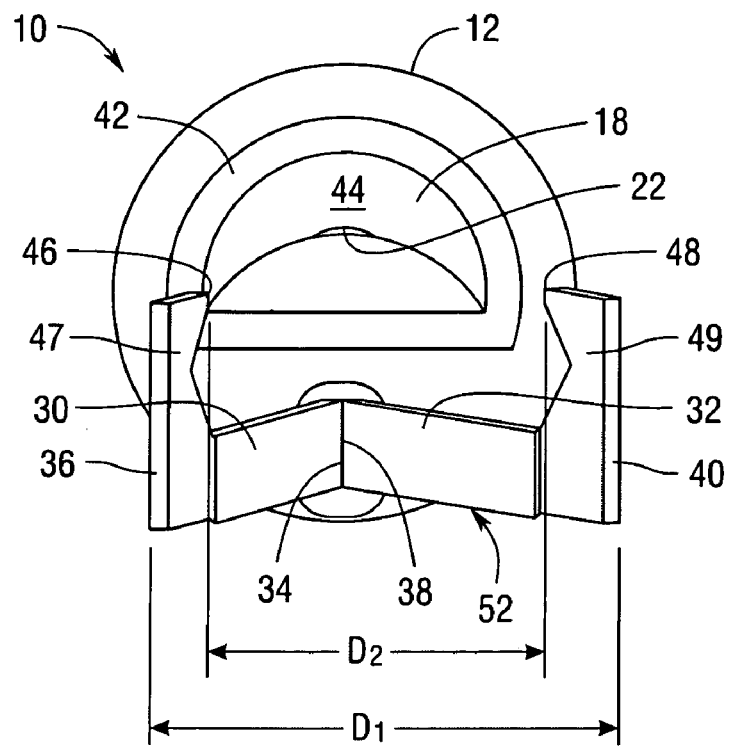
FIG. 3 is a front view of one embodiment of the electrical ablation apparatus shown in FIG. 1.
Figure 4:
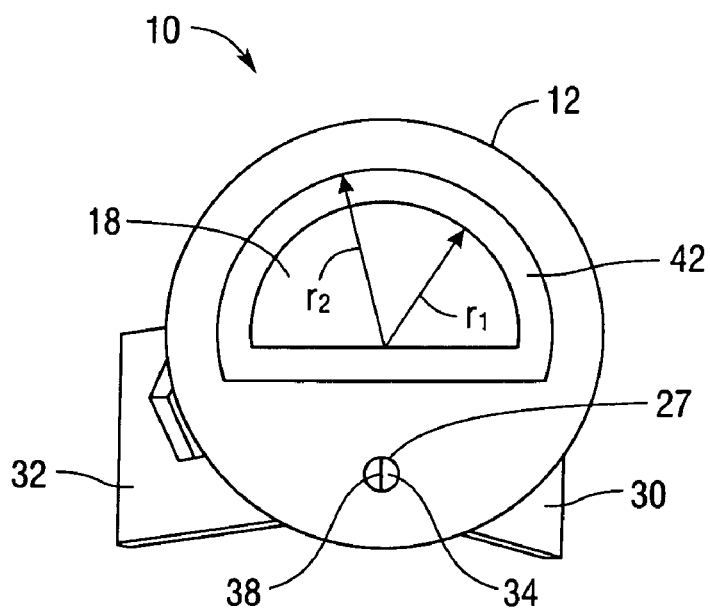
FIG. 4 is a rear view of one embodiment of the electrical ablation apparatus shown in FIG. 1.
Figure 5:
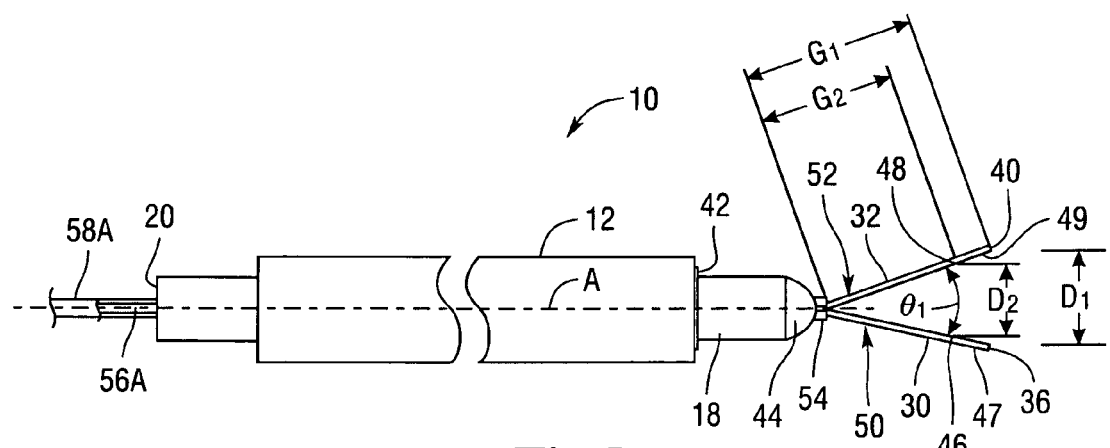
FIG. 5 is a top view of one embodiment of the electrical ablation apparatus shown in FIG. 1.
Figure 6:
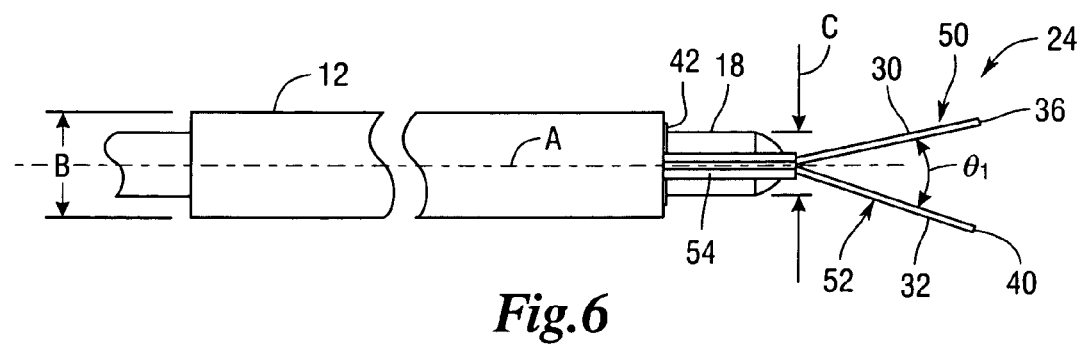
FIG. 6 is a bottom view of one embodiment of the electrical ablation apparatus shown in FIG. 1.

Various embodiments are described to provide an overall understanding of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined, in whole or in part, with the features of other embodiments. Such modifications and variations are intended to be included within the scope of the claims.

It will be appreciated that the terms "proximal" and "distal" are used herein with reference to a clinician manipulating one end of an instrument that protrudes out of a natural orifice (or opening) of the patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the drawings. However, surgical instruments may be used in many orientations and positions, and these terms are not intended to be limiting and absolute.

The various embodiments described herein are directed to electrical ablation devices and techniques. The electrical ablation devices and techniques may be employed to remove various abnormal tissues, including, for example, abnormal masses, tumors, lesions (diseased tissue), and/or adhesions. In one embodiment, the electrical ablation devices comprise electrodes that can be positioned into or in proximity to a treatment region (e.g., target site) inside a patient where there is evidence of abnormal tissue growth. Once positioned, the electrodes are energized by an energy source to deliver electrical current to the treatment region to remove the abnormal tissue. The electrical current flows between the electrodes based on the voltage applied to the electrodes. The electrodes may be energized with direct current (DC) voltages and currents at various polarities and amplitudes or time-varying voltages and currents. Time-varying voltages and currents may be produced by a suitable energy source comprising an electrical waveform generator adapted to deliver electrical energy top the electrodes. The electrical energy produces by the electrical waveform generator may be characterized in terms of frequency, amplitude, pulse width, and polarity. Depending on the diagnostic or therapeutic treatment rendered, the therapy probes may comprise one electrode containing both a cathode and an anode or may contain a plurality of electrodes with at least one serving as a cathode and at least one serving as an anode.

In one embodiment, an electrical ablation device comprising a first and second electrode may be positioned on a distal end of a housing, such as a catheter, suitable for insertion within a patient. In one embodiment, the housing may be a flexible housing. A first electrode is coupled to one pole of an energy source and a second electrode is coupled to another pole of the energy source. The first and second electrodes may be retractable or collapsible within the housing to facilitate insertion of the electrical ablation device inside the patient. For example, the electrical ablation device may be introduced through a narrow working channel of an endoscope, for example. Once the electrical ablation device is positioned near the treatment region, the first and second electrodes are extended distally. In the extended position, the second electrode comprises prongs that separate laterally to form fork-like hook-shaped portions suitable to grasp and hold the abnormal tissue to be ablated. The distance between the distal ends of the first and second electrodes is selected such that no current flows across a gap between the first and second electrodes, when the electrodes are energized at a predetermined energy level. When tissue is located in the fork-like prongs, however, the distance between the distal ends of the first and second electrodes is reduced. This enables current to flow across the gap and produce an electric arc between the distal end of the first electrode and the tissue. The energy delivered by the electric arc is sufficient to ablate the tissue.

FIGS. 1-7 illustrate one embodiment of an electrical ablation device 10 with electrodes in an extended position. In one embodiment, the electrical ablation device 10 comprises a housing 12. The housing 12 comprises a proximal end 14 and a distal end 16. The housing 12 extends along a longitudinal axis "A." In one embodiment, the housing 12 may be formed as an elongated tubular flexible member that is slidably receivable within a flexible portion of an endoscope. The elongated tubular flexible member may be slidably receivable within a working channel of the endoscope. In one embodiment, the elongated tubular flexible member is formed as a flat spring coil pipe.

Figure 10:
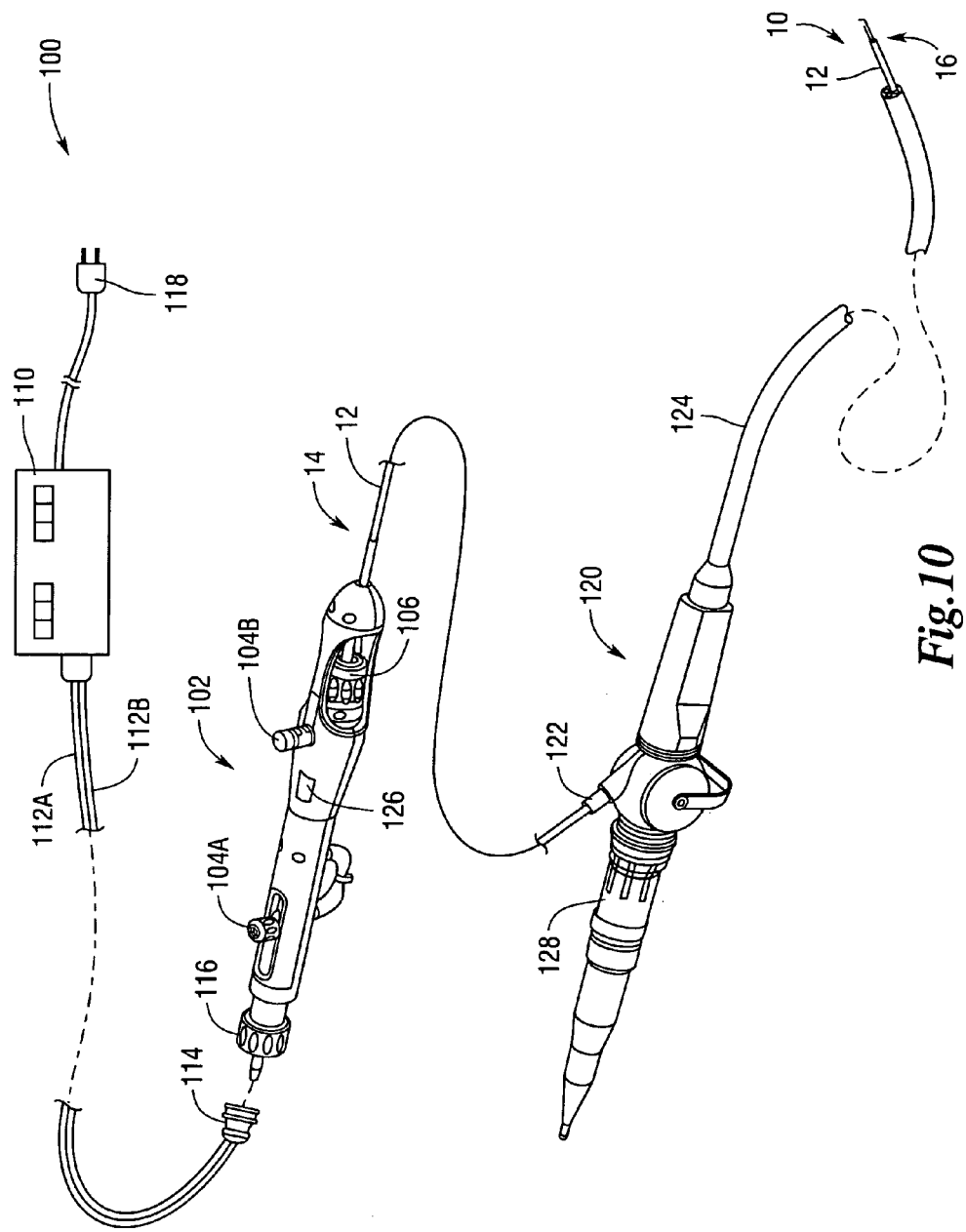
FIG. 10 illustrates one embodiment of an electrical ablation system.
Figure 13:
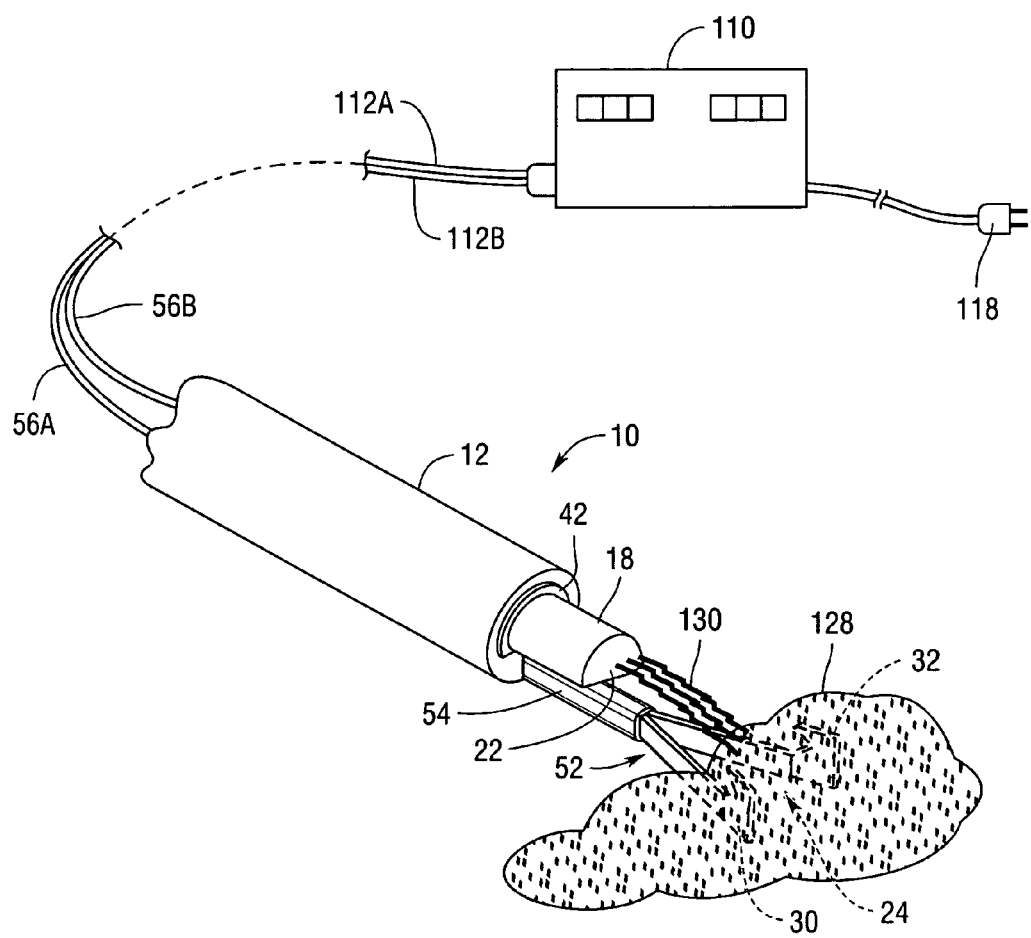
FIG. 13 illustrates one embodiment of the electrical ablation apparatus shown in FIG. 1 with the first and second electrodes in an extended position and engaging tissue being ablated by an electric arc formed between the first electrode and the tissue.

In one embodiment, a first electrode 18 comprises a proximal end 20 and a distal end 22 and is disposed within the housing 12. The proximal end 20 is configured to connect to a first electrically conductive wire 56A. A second electrode 24 comprises a proximal end 26 and a distal end 28. The first and second electrodes 18, 24 may be formed of any suitable electrically conductive materials (e.g., brass, stainless steel) to implement electrically conductive electrodes. The proximal end 26 is configured to connect to a second electrically conductive wire 56B. The first and second electrically conductive wires are adapted to be coupled to an energy source 110 (FIGS. 10, 13). The electrically conductive wire may be received in a channel 27 formed in the housing 12. In one embodiment, the distal end 22 of the first electrode 18 and the distal end 28 of the second electrode 24 are separated by a gap "$G_1$" having a distance when the first and second electrodes 18, 24 are in the extended position as indicated by direction arrow "E." The second electrode 24 comprises a first prong 30 and a second prong 32. The first prong 30 comprises a proximal end 34 and a distal end 36. The second prong 32 comprises a proximal end 38 and a distal end 40. The distal ends 36, 40 of the respective first and second prongs 30, 32 define respective first and second hook portions 47, 49 to grasp the tissue to be ablated. The first and second hook portions 47, 49 define respective first and second proximal ends 46, 48 of the respective first and second prongs 30, 32. A gap "$G_2$" is a distance defined between the distal end 22 of the first electrode 18 and either one of the distal ends 46, 48 of the respective hook portions 47, 49. The proximal ends 20, 26 of the respective first and second prongs 30, 32 are electrically coupled. The distal ends 36, 40 of the respective first and second prongs 30, 32 are separated by a distance "$D_1$" when the second electrode 24 is extended distally in direction "E" and the first and second prongs 30, 32 are fully extended. The proximal ends 46, 48 of the respective first and second hook portions 47, 49 are separated by a distance "$D_2$" when the second electrode 24 is extended distally in direction "E" and the first and second prongs 30, 32 are fully extended. In one embodiment, a first distance defined by the gap "$G_2$" is greater than a second distance defined by the distance "$D_2$."

In one embodiment, the first and second electrodes 18, 24 are slidably extendable in direction "E" and are slidably retractable in direction "R." The first and second electrodes 18, 24 may be slidably extended and retracted independently of each other or may be me slidably extended and retracted dependently, e.g., as a unit. The first electrode 18 is slidably receivable within the housing 12 when it is retracted in direction "R." The first and second prongs 30, 32 comprise respective first and second arms 50, 52 that are slidably movable in directions "R" and "E" within a sleeve 54 formed on the distal end 16 of the housing 12. The first and second prongs 30, 32 are collapsible to be slidably received within the sleeve 54 when the second electrode 24 is retracted in direction "R." The first and second electrodes 18, 24 may be coupled to respective first and second actuator members 58A and 58B to extend and retract the first and second electrodes 18, 24. The first actuator member 58A is coupled to the proximal end 20 of first electrode 18 and is disposed within the housing 12. The second actuator member 58B is coupled to the proximal end 26 of second electrode 24 and is disposed within the channel 27. The actuator members 58A, B may be formed as a solid rod or a tube. The actuator members 58A, B are coupled to an actuator 102 (FIG. 10). The actuator members 58A, B move reciprocally in directions "E" and "R" to respectively extend and retract the first and second electrodes 18, 24.

Figure 7:
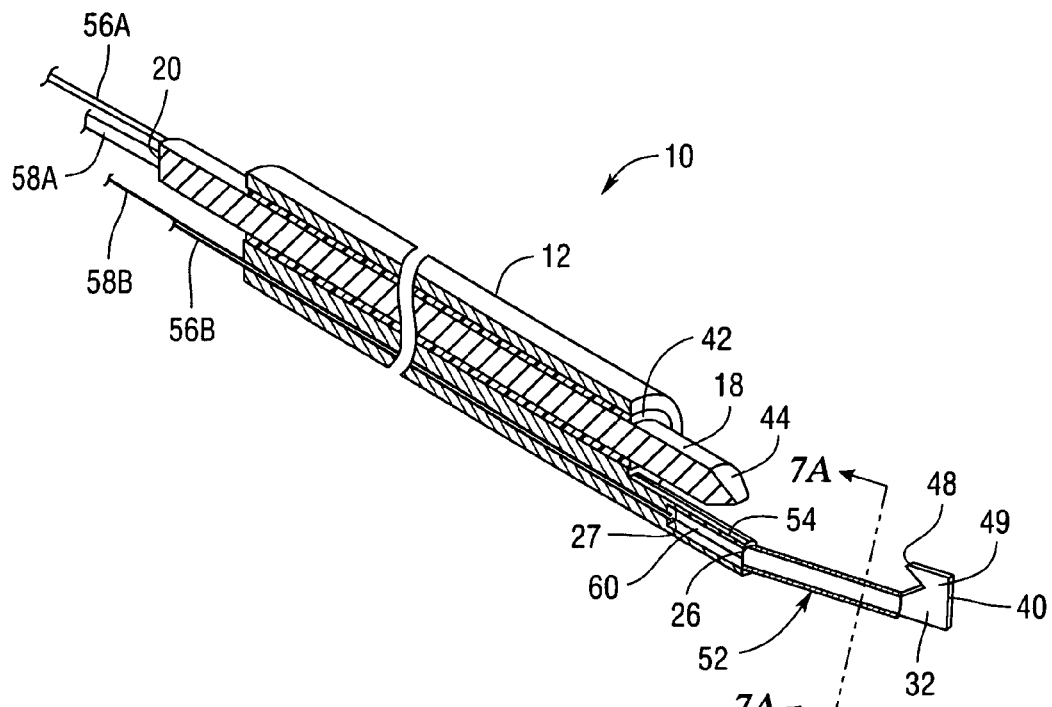
FIG. 7 is a cross-sectional view of one embodiment of the electrical ablation apparatus taken along line 7-7 as shown in FIG. 1.
Figure 7A:
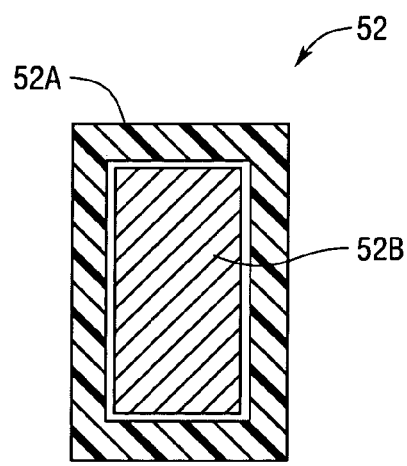
FIG. 7A is a cross-sectional view of an arm portion of a prong of the electrical ablation apparatus taken along line 7A-7A as shown in FIG. 7.

The first and second arms 50, 52 comprise an electrically insulative portion as well as an electrically conductive portion. As shown in FIG. 7A, the second arm 52 comprises an electrically insulative portion 52A and an electrically conductive portion 52B. Although not shown, the first arm 50 comprises an electrically insulative portion similar to the electrically insulative portion 52A of the second arm 52 and an electrically conductive portion similar to the electrically conductive portion 52B of the second arm 52. The electrically insulative portions of the first and second arms 50, 52 may be fabricated from polyimide TEFLON® materials, which provide a substantially lubricious surface and are good electrical insulators.

In one embodiment, the electrical ablation apparatus 10 comprises an electrically insulative sleeve 42 located between the housing 12 and the first electrode 18. The electrically insulative sleeve 42 may be formed of any electrically insulative material to electrically isolate the first electrode 18 from the housing 12 and the second electrode 24. The electrically insulative sleeve 42 may be formed of a substantially frictionless (e.g., lubricious) material. The electrically insulative sleeve 42 may be fabricated from polyimide TEFLON® materials, which provide a substantially lubricious surface and are good electrical insulators.

In one embodiment, the distal end 22 of the first electrode 18 defines a tapered surface 44. In various embodiments, the tapered surface 44 may be formed in a variety of shapes such as any one of a cone, frustro-cone, oblique-cone, right-cone, and right frustro-cone, among other tapered geometric forms. In other embodiments, the distal end 22 of the first electrode 18 may define a blunt surface, a spherical surface, or any suitable geometric form.

In one embodiment, the housing 12 may have a diameter "B" (FIG. 6) of about 2.5 millimeters such that it may be easily inserted in a working channel of an endoscope. For endoscopic applications, the diameter "B" may be selected to be any size that is suitable for insertion within the working channel of the particular endoscope. In one embodiment, the opening "D" between the first and second prongs 30, 32 is about 2 to 4 millimeters. The distance, however, may be selected to be any distance that is suitable for grasping and holding tissue to be ablated. In one embodiment, the gap "$G_1$" between the distal end 22 of the first electrode 18 and the distal end 28 of the extended second electrode 24 is about 3.66 millimeters. The gap "$G_2$" may be about 2.95 millimeters. The gaps "$G_1$" and "$G_2$" may be selected to be any suitable lengths and may be greater than or less than the distances described herein based on energy levels and the materials used to make the first and second electrodes 18, 24, for example. In one embodiment, the angle $\theta_1$ between the first and second prongs 30, 32 is about 40°. The angle $\theta_1$ may be selected to suit any particular implementation. The insulative sleeve 42 may be defined by a first radius $r_1$ and a second radius $r_2$ from the center of the housing 12. In one embodiment, the first radius is about 0.75 millimeters and the second radius $r_2$ is about 0.95 millimeters. Accordingly, in one embodiment, the thickness of the insulative sleeve 42 may be about 0.2 millimeters ($r_2-r_1$). The thickness of the insulative sleeve 42 may be selected based on the energy levels delivered by the energy source 110 (FIGS. 10, 13) so as to provide adequate electrical insulation between the first electrode 18 and the housing 12 and the first and second electrodes 18, 24. Those skilled in the art will appreciate that the dimensions described herein may be modified or selected to suit other specific embodiments taking into account the particular environment, application, and/or implementation of the electrical ablation device 10. Therefore, the embodiments described herein are not limited in this contest.

Figure 8:
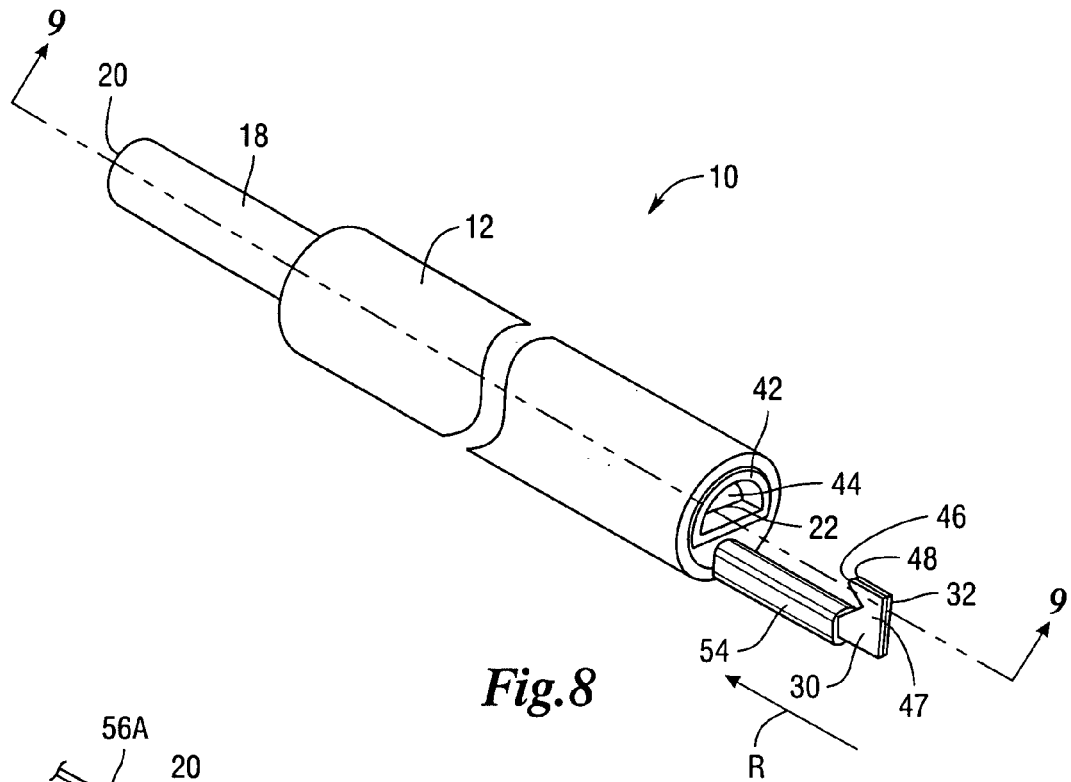
FIG. 8 is a perspective view of one embodiment of the electrical ablation apparatus shown in FIG. 1 with the first and second electrodes in a retracted position.
Figure 9:
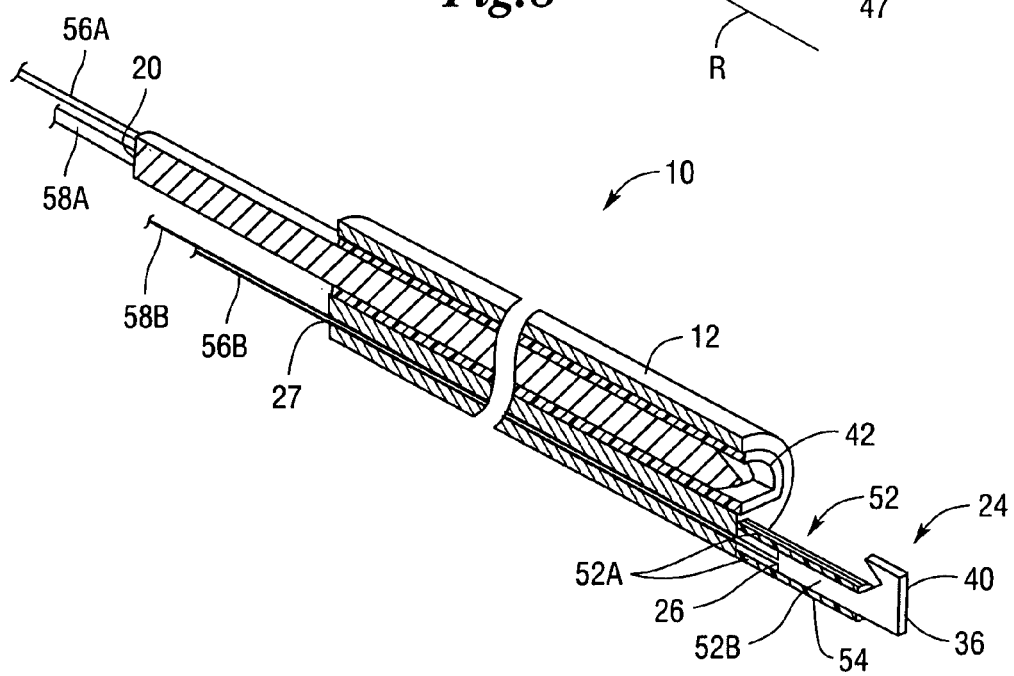
FIG. 9 is a cross-sectional view of one embodiment of the electrical ablation apparatus taken along line 9-9 as shown in FIG. 8.

FIGS. 8 and 9 illustrate the embodiment of the electrical ablation device 10 illustrated in FIGS. 1-7 with the first and second electrodes 18, 24 in a retracted position. As previously discussed, the first and second electrodes 18, 24 may be retracted in direction "R" either independently or in unison depending on the particular implementation of the electrical ablation device 10. In general, the first and second electrodes 18, 24 are retracted in direction "R" to insert the electrical ablation device 10 through the working channel of an endoscope. Once the electrical ablation device 10 is located in proximity of the treatment region, the first and second electrodes 18, 24 are deployed by advancing them in direction "E." As previously discussed, the first and second electrodes 18, 24 may be advanced and retracted using the respective first and second actuator members 58A and 58B.

FIG. 10 illustrates one embodiment of an electrical ablation system 100. In one embodiment, the electrical ablation system 100 comprises an energy source 110, an actuator 102, an endoscope 120, and the electrical ablation device 10. In the illustrated embodiment, the electrical ablation device 10 is electrically coupled to the energy source 110 through an electrical connection in the actuator 102. The housing 12 is introduced into a port 122 in communication with a working channel of the endoscope 120. The electrical ablation device 10 protrudes from the distal end of a flexible endoscopic portion 124 of the endoscope 120.

Referring now to FIGS. 10-13, the energy source 110 is employed to energize the first and second electrodes 18, 24 with an electrical energy level suitable to produce an arc 130 between the distal end 22 of the first electrode 18 and tissue 128 located between the first and second prongs 30, 32. The electric arc 130 is suitable to ablate fibrous tissues such as adhesions growing between internal organs of a patient, for example. The input to the energy source 110 is connected to a commercial power supply by way of a plug 118. The output of the energy source 110 is coupled to the actuator 102 through first and second electrically conductive wires 112A, B, a socket 114, and a plug 116 that is part of the actuator 102. The plug 116 is adapted to electrically connect to the socket 114. The first and second electrically conductive wires 112A, B are electrically connected to the respective first and second electrically conductive wires 56A, B, which are connected to the first and second electrodes 18, 24.

In one embodiment, the energy source 110 comprises a timing circuit to interrupt the output of the energy source 110 and produce a cyclical pattern. The timing circuit may comprise suitable switching elements to produce a cyclical or pulsed output energy signal to drive the electrical ablation device 10. For example, the energy source 110 may produce a series of n pulses suitable to generate the electric arc 130, when the pulsed energy is applied to the first and second electrodes 18, 24.

In one embodiment, the energy source 110 comprises an electrical waveform generator to produce an electrical waveform. The electrical waveform generator produces electric potentials at predetermined frequencies, amplitudes, polarities, and pulse widths. When applied to the first and second electrodes 18, 24, the electric potential causes a current to flow between the distal end 22 of the first electrode 18 and the tissue to generate the electric arc 130.

In one embodiment, the energy source 110 comprises a radio frequency (RF) generator to produce RF waveforms at predetermined frequencies, amplitudes, polarities, and pulse widths. The RF generator may be a conventional, bipolar/monopolar electrosurgical generator such as one of many models commercially available, including Model Number ICC 350, available from Erbe, GmbH.

In one embodiment, the energy source 110 may be a conventional, bipolar/monopolar Pulsed DC generator such as one of many models commercially available, including Model Number ECM 830, available from BTX Molecular Delivery Systems Boston, Mass. In bipolar mode the first electrode 18 may be electrically coupled to one polarity and the second electrode 24 may be electrically coupled to the opposite polarity.

In various embodiments, the energy source 110 produces direct current (DC) electrical pulses delivered at frequencies in the range of 1-20 Hz, amplitudes in the range of ±100 to ±1000 VDC, and pulse widths in the range of 0.01-100 ms. For example, an electrical waveform having amplitude of +500 VDC and pulse duration of 20 ms may be delivered at a pulse repetition rate or frequency of 10 HZ to ablate the tissue 128. In one embodiment, the polarity of the first and second electrodes 18, 24 may be electronically reversed. For example, the polarity of electrical pulses initially delivered at amplitudes in the range of +100 to +1000 VDC may be reversed to -100 to -1000 VDC.

The actuator 102 may be employed to advance and retract the first and second electrodes 18, 24 in the manner previously discussed and to energize the first and second electrodes 18, 24 when the tissue 128 to be ablated is located between the first and second prongs 30, 32. In the illustrated embodiment, the actuator 102 comprises a first slidable element 104A connected to the first actuator member 58A and a second slidable element 104B connected to the second actuator member 58B. The first slidable element 104A is used to advance and retract the first electrode 18 in respective directions "E" and "R" and the second slidable element 104B is used to advance and retract the second electrode 24 in respective directions "E" and "R." A switch 126 is used to energize the first and second electrodes 16, 24 with energy supplied by the energy source 110.

The endoscope 120 comprises a handle 128 and an elongated relatively flexible endoscopic portion 124. The distal end of the endoscopic portion 124 may comprise a light source 132, a viewing port 134, and a working channel 126. The viewing port 132 transmits an image within its field of view to an optical device such as a charge coupled device (CCD) camera within the endoscope 120 so that an operator may view the image on a display monitor (not shown). In the illustrated embodiment, the housing 12 is introduced through a port 122 coupled to the working channel 126 of the endoscope 120. The endoscope 120 comprises a flexible endoscopic portion 124 that is suitable to be inserted inside the patient through various natural orifices. In one embodiment, the endoscope 120 may be a GIF-100 model available from Olympus Corporation. The flexible endoscopic portion 124 of the endoscope 120 may be introduced into the patient trans-anally, trans-vaginally, orally, or through the abdomen via an incision or keyhole. The endoscope 120 assists the surgeon to guide and position the electrical ablation device 10 near the treatment region to treat the diseased tissue 128 growing on organs such as the liver or the intestines.

Figure 11:
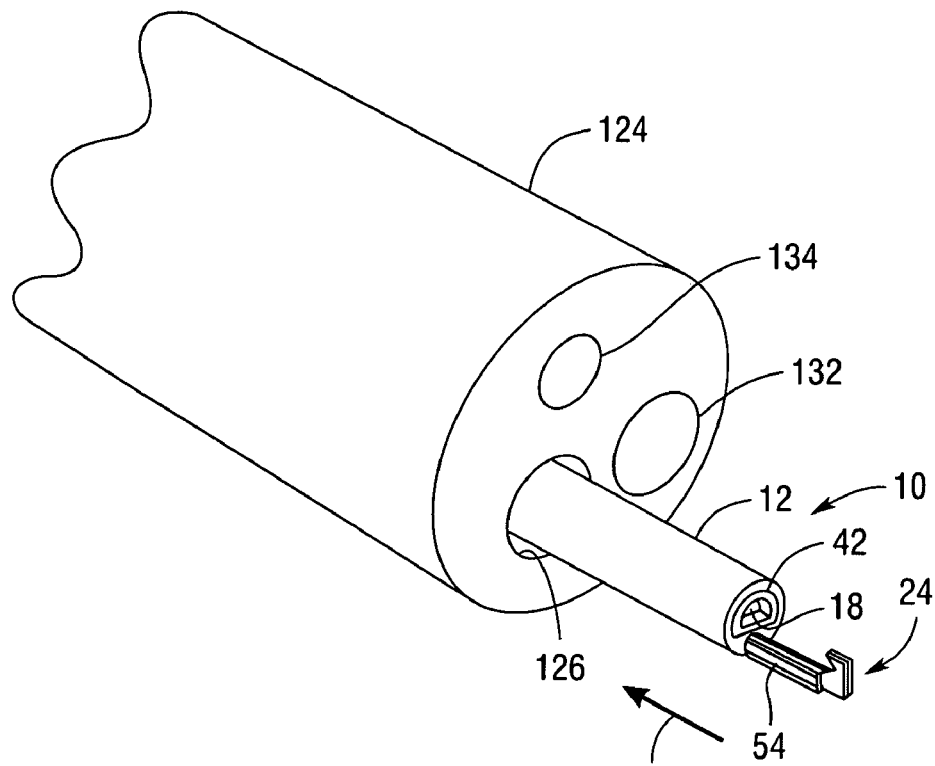
FIG. 11 illustrates one embodiment of the electrical ablation apparatus shown in FIG. 1 with the first and second electrodes in a retracted position protruding from the working channel of an endoscope.
Figure 12:
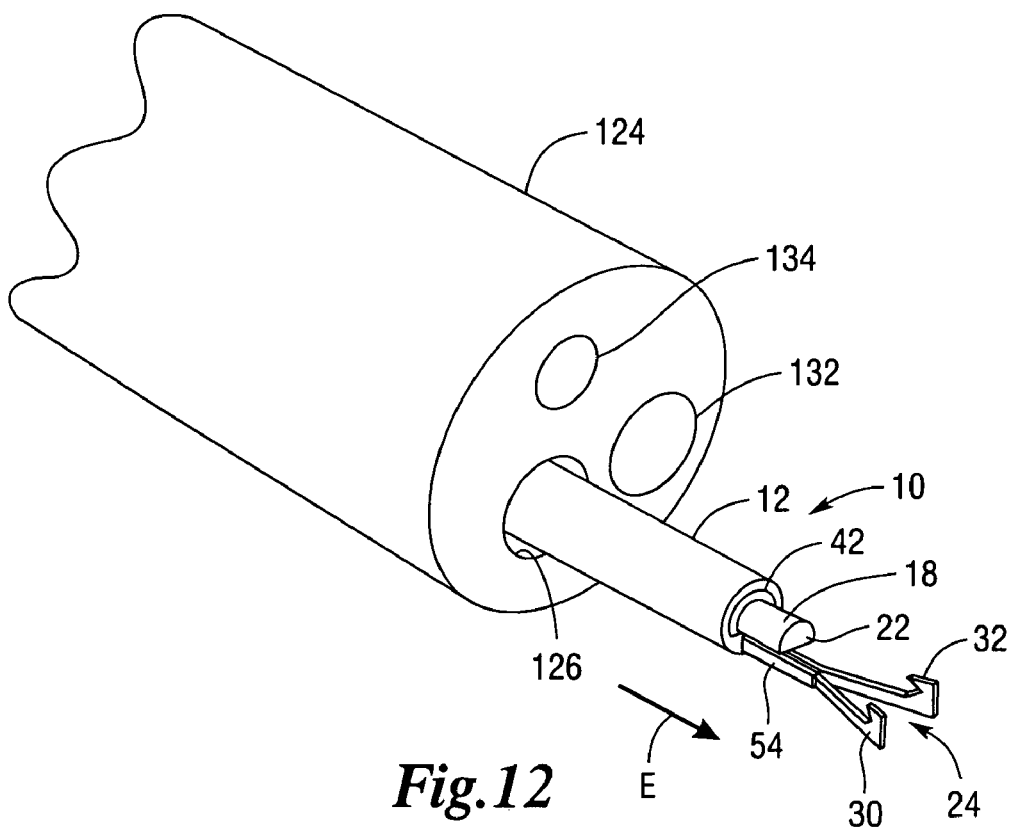
FIG. 12 illustrates one embodiment of the electrical ablation apparatus shown in FIG. 1 with the first and second electrodes in an extended position protruding from the working channel of an endoscope.

As shown in FIG. 11, the first and second electrodes 18, 24 are retracted in direction "R" when the electrical ablation device 10 is introduced through the working channel 126 of the flexible endoscopic portion 124. Once the electrical ablation device 10 is positioned in proximity to the treatment region, the first and second electrodes 18, 24 are extended in direction "E," as shown in FIG. 12.

FIG. 13 illustrates one embodiment of the electrical ablation device 10 shown in FIG. 1 with the first and second electrodes 18, 24 in an extended position and engaging the tissue 128 being ablated by the electric arc 130 formed between the first electrode 18 and the tissue 128. When the first and second electrodes 18, 24 are energized at a predetermined energy level, electric current flows across the gap defined between the distal end 22 of the first electrode 18 and the tissue 128. The current flowing across the gap forms the electric arc 130 that is suitable to ablate the tissue 128. The electric arc 130 is formed when the tissue 128 is located in the opening defined between the distal end 22 of the first electrode 18 and the first and second prongs 30, 32.

The various embodiments of the electrical ablation device 10 described herein may be introduced within a patient using minimally invasive surgical techniques or conventional open surgical techniques. In some instances in may be advantageous to introduce the electrical ablation device 10 into the patient using a combination of minimally invasive and open surgical techniques. Minimally invasive techniques provide more accurate and effective access to the treatment region for diagnostic and treatment procedures. Some minimally invasive procedures are performed by the introduction of various medical devices into the patient through a natural opening of the patient. These procedures are known as Natural Orifice Translumenal Endoscopic Surgery (NOTES™). Accordingly, the various embodiments of the electrical ablation device 10 described herein may be used in endoscopic and/or laparoscopic surgical procedures, conventional laparotomies, or any combinations thereof.

To reach the treatment region, in one embodiment, the electrical ablation device 10 may be inserted through a natural orifice of the body. Natural orifices include the mouth, anus, and/or vagina, for example. Internal organs may be reached using trans-organ or trans-lumenal surgical procedures. In a typical natural orifice endoscopic translumenal procedure (e.g., NOTES™), the flexible endoscopic portion 124 of the endoscope 120 may be introduced into the patient through one or more natural orifices to view the treatment region using direct line-of-sight, a camera, or other visualization devices. The working channel 126 of the endoscope 120 is used for introducing surgical devices, such as the electrical ablation device 10, to the treatment region to perform key surgical activities (KSA). A KSA includes ablating abnormal fibrous tissue generally known as adhesions.

Figure 14:
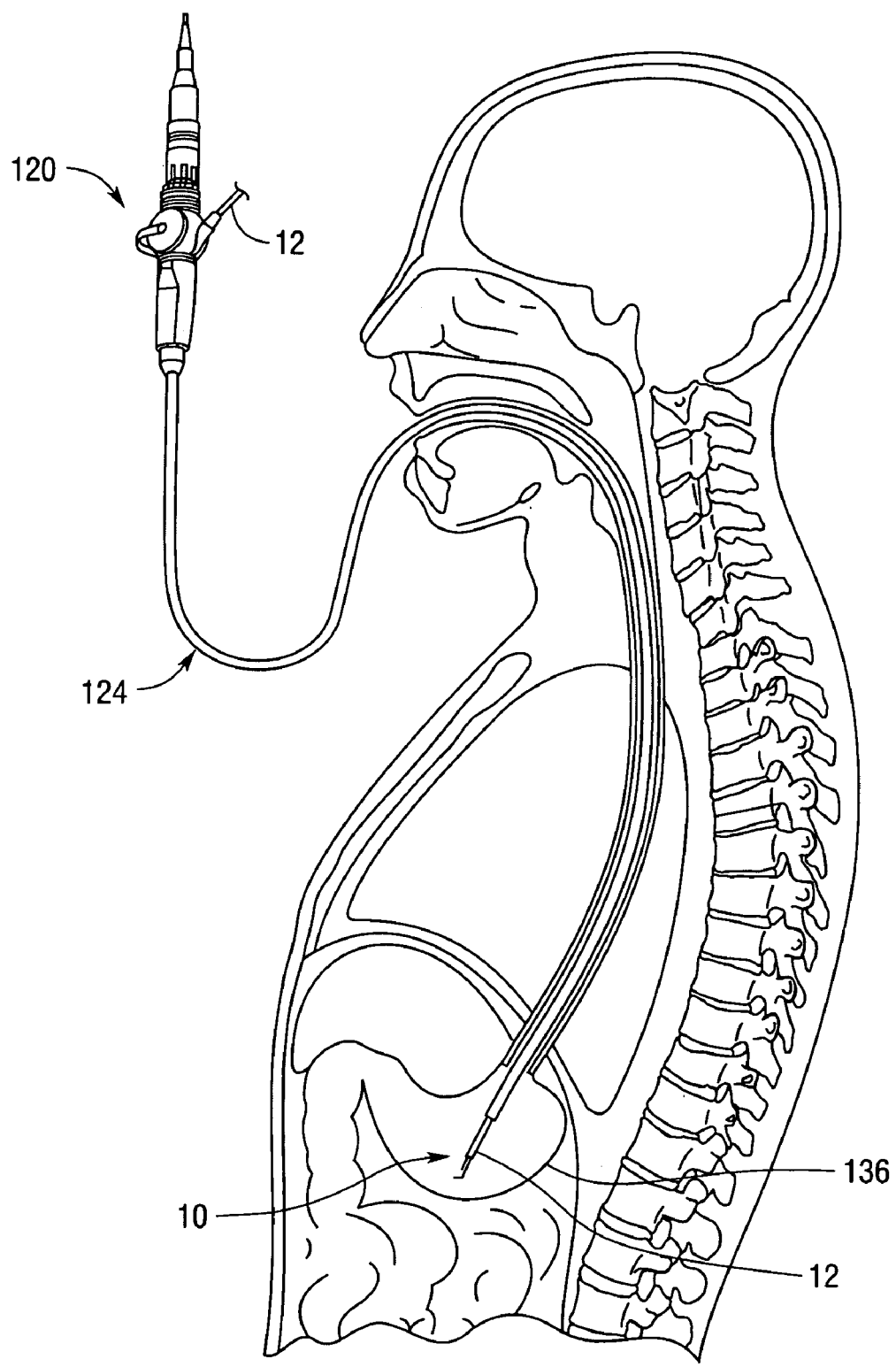
FIG. 14 illustrates a flexible endoscopic portion of a gastroscope inserted into the upper gastrointestinal tract of the patient and into the stomach to position one embodiment of the electrical ablation apparatus shown in FIG. 1 for ablating tissue therein.

FIG. 14 illustrates the flexible endoscopic portion 124 of the endoscope 120 (e.g., gastroscope) inserted into the upper gastrointestinal tract of a patient and into the stomach 136 to position the electrical ablation device 10 in proximity of abnormal tissue to be ablated. With reference to FIGS. 10-14, the flexible endoscopic portion 124 of the endoscope 120 is positioned in proximity of the treatment region. The electrical ablation device 10 is inserted through the working channel 126 of the flexible endoscopic portion 124 of the endoscope 120. During the insertion phase, the electrical ablation device is in the retracted. Once the electrical ablation device 10 is positioned in the treatment region, the first and second electrodes 18, 24 are extended through the distal end of the tubular flexible member 12. In the fully extended position, the first and second prongs 30, 32 of the second electrode 24 spring open and separate to form a hook-like fork at the distal end of the second electrode 24. The tissue 128 to be ablated is grasped by the first and second prongs 30, 32. The first and second electrodes 18, 24 are energized by the energy source 110 to ablate the tissue 128 with the electric arc 130 formed by electric current flowing between the distal end 22 of the first electrode 18 and the tissue 128.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, said to be incorporated by reference herein, but which conflicts with existing definitions, statements, or other disclosure material set forth herein will only be incorporated to the extent that no conflict arises between that incorporated material and the existing disclosure material.

The invention claimed is:

1. An electrical ablation apparatus, comprising:
   a housing comprising a proximal end and a distal end, a flexible housing extending along a longitudinal axis;
   a first electrode comprising a proximal end and a distal end is disposed within the housing, the proximal end is adapted to couple to an energy source; and
   a second electrode comprising a proximal end and a distal end is disposed within the flexible housing, the proximal end is adapted to couple to an energy source, wherein the distal ends of the first and second electrodes are separated by a gap, the second electrode comprising:
   a first prong comprising a proximal end and a distal end; and
   a second prong comprising a proximal end and a distal end, the first and second prongs are electrically coupled at the proximal end and are configured to separate and define an opening when the second electrode is extended distally;
   wherein the size of the opening is selectively adjustable such that when the first and second electrodes are energized by the energy source at a predetermined energy level, an electric current suitable to ablate tissue located within the opening flows across the gap and forms an electric arc between the distal end of the first electrode and the tissue.

2. The electrical ablation apparatus of claim 1, wherein the first electrode is movable to retract within the flexible housing.

3. The electrical ablation apparatus of claim 1, comprising an electrically insulative sleeve between the flexible housing and the first electrode.

4. The electrical ablation apparatus of claim 1, wherein the distal end of the first electrode defines a tapered surface.

5. The electrical ablation apparatus of claim 4, wherein the tapered surface defines any one of a conical, frustro-conical, oblique-conical, right-conical, and right frustro-conical surface.

6. The electrical ablation apparatus of claim 1, wherein the distal end of the first electrode defines blunt surface.

7. The electrical ablation apparatus of claim 1, wherein the distal end of the first electrode defines a spherical surface.

8. The electrical ablation apparatus of claim 1, wherein the second electrode is movable to retract within a sleeve located at the distal end the housing.

9. The electrical ablation apparatus of claim 8, wherein the first and second prongs are collapsible to be slidably received within the sleeve when the second electrode is retracted.

10. The electrical ablation apparatus of claim 1, wherein the distal ends of the first and second prongs define respective first and second hooks to grasp tissue to be ablated.

11. The electrical ablation apparatus of claim 1, wherein the first and second prongs of the second electrode extend distally at an angle relative to the longitudinal axis.

12. The electrical ablation apparatus of claim 1, wherein the proximal end of the first prong of the second electrode is located at a first distance from the distal end of the first electrode and the proximal end of the second prong of the second electrode is located at the first distance from the distal end of the first electrode, and wherein the first distance is greater than a second distance defined between the proximal ends of the first and second prongs of the second electrode.

13. The electrical ablation apparatus of claim 1, wherein the housing is formed as an elongated tubular flexible member that is slidably receivable within a flexible portion of an endoscope.

14. The electrical ablation apparatus of claim 13, wherein the elongated tubular flexible member is slidably receivable within a working channel of the flexible portion of the endoscope.

15. An electrical ablation system, comprising:
   an energy source;
   an electrical ablation apparatus coupled to the energy source, the electrical ablation apparatus comprising:
   a housing comprising a proximal end and a distal end, the housing extending along a longitudinal axis;
   a first electrode comprising a proximal end and a distal end is disposed within the housing, the proximal end is configured to couple to the energy source; and
   a second electrode comprising a proximal end and a distal end is disposed within the housing, the proximal end is configured to couple to the energy source, the distal ends of the first and second electrodes are separated by a gap, the second electrode comprising:
   a first prong comprising a proximal end and a distal end; and
   a second prong comprising a proximal end and a distal end, the first and second prongs are electrically coupled at the proximal end and are configured to separate and define an opening when the second electrode is extended distally;
   wherein the size of the opening is selectively adjustable such that when the first and second electrodes are energized by the energy source at a predetermined energy level, an electric current suitable to ablate tissue located within the opening flows across the gap and forms an electric arc between the distal end of the first electrode and the tissue.

16. The electrical ablation system of claim 15, wherein the first electrode is movable to retract within the housing.

17. The electrical ablation system of claim 15, wherein the second electrode is movable to retract within a sleeve located at the distal end of the housing.

18. A method of endoscopically ablating tissue, the method comprising:
   inserting a portion of an endoscope into a natural opening of a patient to a target site;
   inserting an electrical ablation apparatus through a working channel of the portion of the endoscope, the electrical ablation apparatus comprising:
   a housing comprising a proximal end and a distal end, the housing extending along a longitudinal axis;

a first electrode comprising a proximal end and a distal end is disposed within the housing, the proximal end is configured to connect to a first electrically conductive wire; and a second electrode comprising a proximal end and a distal end is disposed within the housing, the proximal end is configured to connect to a second electrically conductive wire, the distal ends of the first and second electrodes are separated by a gap, the second electrode comprising:

a first prong comprising a proximal end and a distal end; and a second prong comprising a proximal end and a distal end, the first and second prongs are electrically coupled at the proximal end and are configured to separate and define an opening when the second electrode is extended distally;

extending the distal ends of the first and second electrodes through the distal end of the elongated tubular member to separate the first and second prongs; receiving tissue to be ablated between the first and second prongs;

energizing the first and second electrodes; and ablating the tissue located in the gap with an electric current that forms an electric arc between the first electrode and the tissue.

* * * * *